(12) United States Patent
Eisenschmid et al.

(10) Patent No.: US 9,688,598 B2
(45) Date of Patent: Jun. 27, 2017

(54) HYDROFORMYLATION PROCESS

(71) Applicant: Dow Technology Investments LLC, Midland, MI (US)

(72) Inventors: Thomas C. Eisenschmid, South Charleston, WV (US); Morteza Mokhtarzadeh, Charleston, WV (US); Cloid R. Smith, III, Charleston, WV (US); Michael C. Becker, Dickinson, TX (US); George R. Phillips, South Charleston, WV (US); Michael A. Brammer, Freeport, TX (US); Glenn A. Miller, South Charleston, WV (US); Rick B. Watson, Missouri City, TX (US); Irvin B. Cox, The Villages, FL (US); Edward A. Lord, London (GB); Martin Smidt, London (GB)

(73) Assignee: DOW TECHNOLOGY INVESTMENTS LLC, Midland, MI (US)

( * ) Notice: Subject to any disclaimer, the term of this patent is extended or adjusted under 35 U.S.C. 154(b) by 0 days.

(21) Appl. No.: 15/032,068

(22) PCT Filed: Dec. 9, 2014

(86) PCT No.: PCT/US2014/069190
§ 371 (c)(1),
(2) Date: Apr. 26, 2016

(87) PCT Pub. No.: WO2015/094781
PCT Pub. Date: Jun. 25, 2015

(65) Prior Publication Data
US 2016/0257635 A1   Sep. 8, 2016

Related U.S. Application Data

(60) Provisional application No. 61/918,353, filed on Dec. 19, 2013.

(51) Int. Cl.
| | | |
|---|---|---|
| C07C 45/50 | (2006.01) |
| B01J 31/00 | (2006.01) |
| C07C 45/82 | (2006.01) |
| B01J 31/24 | (2006.01) |
| C07C 45/78 | (2006.01) |

(52) U.S. Cl.
CPC .............. *C07C 45/50* (2013.01); *B01J 31/24* (2013.01); *C07C 45/78* (2013.01); *C07C 45/82* (2013.01); *B01J 2231/321* (2013.01); *B01J 2531/822* (2013.01); *Y02P 20/582* (2015.11)

(58) Field of Classification Search
CPC ................. C07C 45/50; B01J 31/24
USPC .............................. 568/454, 456
See application file for complete search history.

(56) References Cited

U.S. PATENT DOCUMENTS

| | | | |
|---|---|---|---|
| 3,415,906 A | 12/1968 | Shepard et al. |
| 3,527,809 A | 9/1970 | Pruett et al. |
| 4,148,830 A | 4/1979 | Pruett et al. |
| 4,166,773 A | 9/1979 | Higley et al. |
| 4,247,486 A | 1/1981 | Brewester et al. |
| 4,262,142 A * | 4/1981 | Sherman, Jr. ........... C07C 45/50 |
| | | | 568/454 |
| 4,329,507 A | 5/1982 | Takeda et al. |
| 4,400,547 A | 8/1983 | Dawes et al. |
| 4,518,809 A | 5/1985 | Forster et al. |
| 4,528,403 A | 7/1985 | Tano et al. |
| 4,567,302 A | 1/1986 | Sivaramakrishnan |
| 4,567,306 A | 1/1986 | Dennis et al. |
| 4,593,127 A | 6/1986 | Bunning et al. |
| 4,599,206 A | 7/1986 | Billig et al. |
| 4,668,651 A | 5/1987 | Billig et al. |
| 4,694,109 A | 9/1987 | Devon et al. |
| 4,717,775 A | 1/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,835,299 A | 5/1989 | Maher et al. |
| 4,885,401 A | 12/1989 | Billig et al. |
| 5,102,505 A | 4/1992 | Sorensen |
| 5,105,018 A | 4/1992 | Miyazawa et al. |
| 5,110,990 A | 5/1992 | Blessing et al. |
| 5,113,022 A | 5/1992 | Abatjoglou et al. |
| 5,179,055 A | 1/1993 | Wink et al. |
| 5,202,297 A | 4/1993 | Lorz et al. |
| 5,235,113 A | 8/1993 | Sato et al. |
| 5,254,741 A | 10/1993 | Lorz et al. |
| 5,264,616 A | 11/1993 | Roeper et al. |
| 5,277,532 A | 1/1994 | Pazzaglia |
| 5,288,918 A | 2/1994 | Maher et al. |
| 5,312,996 A | 5/1994 | Packett |
| 5,332,846 A | 7/1994 | Devon et al. |

(Continued)

FOREIGN PATENT DOCUMENTS

| | | |
|---|---|---|
| CN | 101293818 A | 10/2008 |
| CN | 101565353 A | 10/2009 |
| CN | 102826969 A | 12/2012 |
| EP | 0052999 A1 | 6/1982 |
| EP | 1008580 A1 | 6/2000 |
| GB | 1120277 A | 7/1968 |
| JP | 2006/306815 A | 11/2006 |
| JP | 3864668 B2 | 1/2007 |
| WO | WO-80/01691 A1 | 8/1980 |
| WO | WO-2007/078859 A2 | 7/2007 |
| WO | WO-2008/071508 A1 | 6/2008 |
| WO | WO-2010/003073 A1 | 1/2010 |
| WO | WO-2011/087690 A1 | 7/2011 |
| WO | WO-2012/009717 A1 | 1/2012 |
| WO | WO-2012/064586 A1 | 5/2012 |

OTHER PUBLICATIONS

Sansar, Undergraduate Journal of Mathematical Modeling: One + Two, 2010, vol. 2, Issue 2, Article 9, p. 1-14.

(Continued)

*Primary Examiner* — Sikarl Witherspoon

(57) ABSTRACT

A multi-reaction train hydroformylation process wherein a common product-catalyst separation zone is employed.

15 Claims, 8 Drawing Sheets

(56) References Cited

U.S. PATENT DOCUMENTS

| | | |
|---|---|---|
| 5,360,938 A | 11/1994 | Babin et al. |
| 5,364,950 A | 11/1994 | Babin et al. |
| 5,391,801 A | 2/1995 | Sato et al. |
| 5,410,091 A * | 4/1995 | Nall .................. C07C 45/50 568/454 |
| 5,430,194 A | 7/1995 | Barner et al. |
| 5,491,266 A | 2/1996 | Babin et al. |
| 5,527,950 A | 6/1996 | Hansen et al. |
| 5,648,554 A | 7/1997 | Mori et al. |
| 5,681,473 A | 10/1997 | Miller et al. |
| 5,710,344 A | 1/1998 | Breikss et al. |
| 5,728,893 A | 3/1998 | Becker et al. |
| 5,731,472 A | 3/1998 | Leung et al. |
| 5,731,473 A | 3/1998 | Bryant et al. |
| 5,741,942 A | 4/1998 | Bryant et al. |
| 5,741,944 A | 4/1998 | Bryant et al. |
| 5,744,649 A | 4/1998 | Bryant et al. |
| 5,789,625 A | 8/1998 | Bryant et al. |
| 5,929,289 A | 7/1999 | Abatjoglou et al. |
| 6,265,620 B1 | 7/2001 | Urata et al. |
| 6,440,891 B1 | 8/2002 | Maas et al. |
| 6,846,960 B2 | 1/2005 | Tolleson et al. |
| 6,995,292 B2 | 2/2006 | Tolleson et al. |
| 7,009,068 B2 | 3/2006 | Schmutzler et al. |
| 7,145,042 B2 | 12/2006 | Volland et al. |
| 7,196,230 B2 | 3/2007 | Peng et al. |
| 7,262,330 B2 | 8/2007 | Ueda et al. |
| 7,329,783 B2 | 2/2008 | Mul |
| 7,586,010 B2 | 9/2009 | Liu et al. |
| 7,615,645 B2 | 11/2009 | Volland et al. |
| 7,674,937 B2 | 3/2010 | Tolleson et al. |
| 7,872,156 B2 | 1/2011 | Liu et al. |

OTHER PUBLICATIONS

Duerksen, J. Polymer Sci.: Part C, 1968, vol. 25, p. 155-166.
CRC Handbook of Chemistry and Physics, 72nd Ed. (1991-1992) CRC Press, at p. I-10.
PCT/US2014/069190, International Preliminary Report on Patentability dated Mar. 11, 2016.
PCT/US2014/069190, Written Opinion dated Jun. 25, 2015.
PCT/US2014/069190, Search Report dated Jun. 25, 2015.

* cited by examiner

HYDROFORMYLATION PROCESS

BACKGROUND OF THE INVENTION

The invention relates to a process for the hydroformylation of olefins to produce aldehydes.

It is often desirable to feed two or more olefins at the same hydroformylation facility. In some cases, both olefins are fed to the same reactor. This process, commonly referred to as a "co-feed" process, allows capital savings compared to having separate, complete production trains for each olefin. The co-feed process shares a hydroformylation reactor and product-catalyst separation equipment, and then downstream refining separates the products for further processing. Examples of this process are disclosed in EP 0 052 999, GB 1,120,277, WO 1980/001691, U.S. Pat. No. 4,262,142, Ex. 13 of U.S. Pat. No. 4,400,547 and U.S. Pat. No. 5,312,996.

Inherent to co-feed operation are problems, compared to operations using 2 separate reactor trains, with balancing the reactors with variable feed rates, such as when one feed supply is reduced, and maintaining product isomer ratios. In the first case, a reduction in the amount of the more highly reactive olefin, e.g., ethylene, greatly impacts heat generation, which may make the reactors unstable. Conversely, a reduction in the amount of the less reactive olefin feed will give a first reactor enriched with highly reactive olefin and the reactor coolers may not be able to maintain steady state operation. Changes in feed composition may also impact reactor stability and catalyst performance. For example, an inhibitor in one feed will impact the performance for the entire production system.

Another problem with co-feed operation, compared to operations using 2 separate reactor trains, is that the reactor volume occupied by the product of the more reactive olefin is not productive, and the extra time the product spends in the reactor encourages side reactions such as heavies formation and ligand degradation. Sudden changes in feed quality or availability can generate very extreme catalyst concentrations that may impact overall plant stability.

It is well known that the ratio of linear and branched aldehyde isomer products, commonly referred to as the N:I ratio, is dependent on a number of factors including ligand identity and concentration, usually defined as the ligand-to-rhodium ratio, temperature, and CO and $H_2$ partial pressures. In a co-feed system, these conditions are the same for both reacting olefins, although the desired N:I product ratio for the two products may differ greatly, so that the conditions are a compromise rather than what is optimal for each product.

Based on these concerns, it is common practice to build separate production trains for each olefin despite the additional capital cost. It would be desirable to have a multi-reaction-train hydroformylation process that could operate using a common product-catalyst separation zone, e.g., a vaporizer, as this would result in capital cost savings yet exhibit robust operational stability.

SUMMARY OF THE INVENTION

The invention is such a process comprising
  contacting in a first reactor train CO, $H_2$, and a first feed stream comprising an
  olefin in the presence of a hydroformylation catalyst in a reaction fluid under hydroformylation conditions sufficient to form at least one aldehyde product,
  contacting in at least one additional reactor train CO, $H_2$, and at least one additional feed stream comprising an olefin, in the presence of a hydroformylation catalyst in a reaction fluid under hydroformylation conditions sufficient to form at least one aldehyde product, wherein the additional reactor train is operated in parallel to the first train, and
  removing an effluent stream comprising the reaction fluid from each train and passing the effluent streams from at least 2 reactor trains to a common product-catalyst separation zone.

Surprisingly, a process wherein the olefins are fed to separate trains that share a common product-catalyst separation zone and downstream equipment can realize most of the desired capital savings of a traditional co-feed system while avoiding its pitfalls.

DETAILED DESCRIPTION OF THE INVENTION

Figure 1:
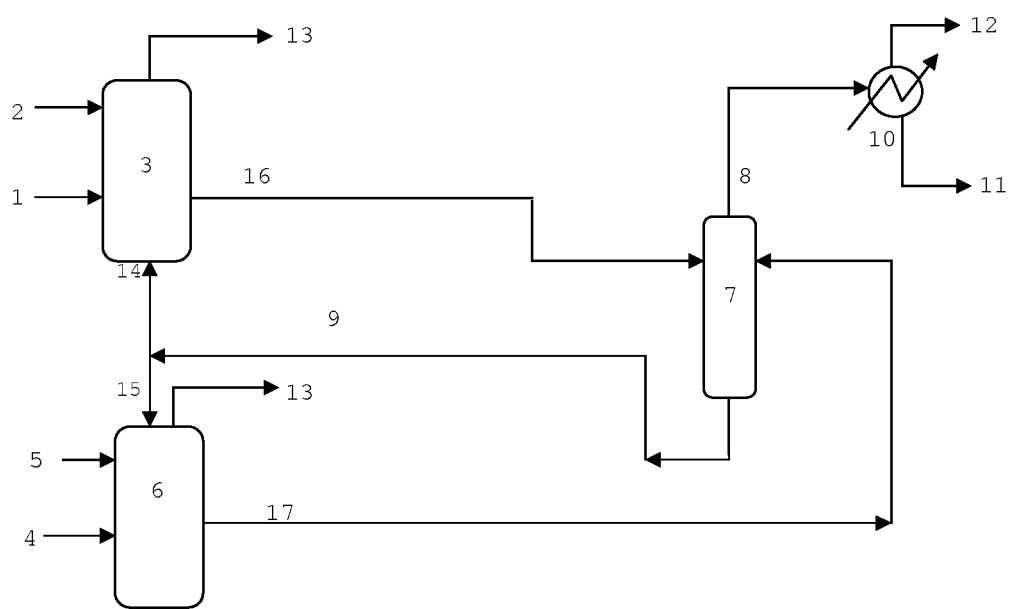
FIG. 1 is a schematic of an hydroformylation process that employs a common product-catalyst separation zone, e.g., a thin film vaporizer.

The disclosed process comprises contacting CO, $H_2$, and at least one olefin under hydroformylation conditions sufficient to form at least one aldehyde product in the presence of a catalyst comprising, as components, a transition metal and an organophosphorous ligand.

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety, or its equivalent US version is so incorporated by reference, especially with respect to the disclosure of definitions, to the extent not inconsistent with any definitions specifically provided in this disclosure, and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range, e.g., 1 to 5 includes 1, 1.5, 2, 2.75, 3, 3.80, 4, 5, etc. For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic, with or without heteroatoms, and cyclic, branched and unbranched, carbocyclic and heterocyclic, aromatic and nonaromatic organic compounds, which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but is not limited to, all hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes. The aldehydes may be asymmetric or non-asymmetric.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds, which may be dissolved and/or suspended, formed in the reaction. The reaction fluid can encompass, but is not limited to, (a) a fluid in a reactor, (b) a fluid stream on its way to a separation zone, (c) a fluid in a separation zone, (d) a recycle stream, (e) a fluid withdrawn from a reaction zone or separation zone, (f) a withdrawn fluid being treated with an acid removal system such as an extractor or other immiscible fluid contacting system, (g) a treated or untreated fluid returned to a reaction zone or separation zone, (h) a fluid in an external cooler, and (i) ligand decomposition products and components derived from them, such as oxides, sulfides, salts, oligomers, and the like.

Any suitable technique for separating the product from catalyst in the reactor train effluents can be employed. Unit operations suitable for use in the product-catalyst separation zone are well known to those skilled in the art and can comprise, for example, solvent extraction, membrane separation, crystallization, phase separation or decanting, filtration, distillation, and the like, and any combination thereof. Examples of distillation include flashing, wiped film evaporation, falling film evaporation, thin film evaporation, and distillation in any other type of conventional distillation equipment. Examples of membrane separation processes are disclosed in U.S. Pat. No. 5,430,194 and U.S. Pat. No. 5,681,473. For the purposes of the invention, the term "vaporization" will be used to encompass these unit operations, and the term "vaporizer" is used synonymously with "product-catalyst separation zone."

"Hydrolyzable organophosphorous ligands" are trivalent phosphorous ligands that contain at least one P—Z bond wherein Z is oxygen, nitrogen, chlorine, fluorine or bromine Examples include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligands may include chelate structures and/or may contain multiple P—Z moieties such as polyphosphites, polyphosphoramidites, etc. and mixed P—Z moieties such as phosphite-phosphoramidites, flurophosphite-phosphites, and the like.

The term "free ligand" means ligand that is not complexed with, tied to or bound to, the metal, e.g., metal atom, of the complex catalyst.

Hydrogen and carbon monoxide are required for the process. These may be obtained from any suitable source, including petroleum cracking and refinery operations. Syngas mixtures are preferred as a source of hydrogen and CO.

Syngas (from synthesis gas) is the name given to a gas mixture that contains varying amounts of CO and $H_2$. Production methods are well known and include, for example: (1) steam reforming and partial oxidation of natural gas or liquid hydrocarbons and (2) the gasification of coal and/or biomass. Hydrogen and CO typically are the main components of syngas, but syngas may contain carbon dioxide and inert gases such as $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO molar ratio for chemical production is between 3:1 and 1:3 and usually is targeted to be between about 1:2 and 2:1 for most hydroformylation applications.

Each reactor train has its own olefin feed stream. The feed streams may be the same or different. In one embodiment of the invention, the first and second feed streams comprise different olefin compositions. For example, the first feed stream may comprise ethylene and/or propylene as a first olefin, and the second feed stream may comprise at least one higher olefin. For the purposes of the invention, a higher olefin is an olefin that has 3 or more carbon atoms. As a practical matter, the higher olefin may contain small amounts of ethylene. In one embodiment of the invention, the higher olefin comprises less than 40 wt. percent of ethylene. In another embodiment of the invention, the higher olefin comprises less than 2 wt. percent of ethylene.

The substituted or unsubstituted olefinic unsaturated starting material reactants that may be employed in the hydroformylation process include both optically active (prochiral and chiral) and non-optically active (achiral) olefinic unsaturated compounds containing from 2 to 40, preferably 3 to 20, carbon atoms. Such olefinic unsaturated compounds can be terminally or internally unsaturated, straight-chain, branched chain or cyclic. Olefin mixtures, such as obtained from the oligomerization of propene, butene, isobutene, etc., such as so called dimeric, trimeric or tetrameric propylene and the like, as disclosed, for example, in U.S. Pat. Nos. 4,518,809 and 4,528,403, can be employed. Moreover, such olefin compounds may further contain one or more additional ethylenic unsaturated groups, and mixtures of two or more different olefinic unsaturated compounds may be employed as the starting hydroformylation material if desired. For example, commercial alpha olefins containing four or more carbon atoms may contain amounts of corresponding internal olefins and/or trisubstituted olefins and/or their corresponding saturated hydrocarbon and that such commercial olefins need not necessarily be purified from same prior to being hydroformylated. Illustrative mixtures of olefinic starting materials that can be employed in the hydroformylation reactions include, for example, mixed butenes, e.g., Raffinate I and II. Further such olefinic unsaturated compounds and the corresponding aldehyde products derived therefrom may also contain one or more groups or substituents that do not unduly adversely affect the hydroformylation process or the process of this invention such as described, for example, in U.S. Pat. Nos. 3,527,809, 4,769,498 and the like.

Most preferably, the invention is especially useful for the production of non-optically active aldehydes by hydroformylating achiral alpha-olefins containing from 2 to 30, preferably 3 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene as well as, 1,3-dienes, butadiene, alkyl alkenoates, e.g., methyl pentenoate, alkenyl alkanoates, alkenyl alkyl ethers, alkenols, e.g., pentenols, alkenals, e.g., pentenals, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, and the like.

Prochiral and chiral olefins useful in the asymmetric hydroformylation that can be employed to produce enantiomeric aldehyde mixtures include those represented by the formula:

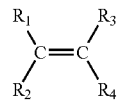

wherein $R_1$, $R_2$, $R_3$ and $R_4$ are the same or different, provided $R_1$ is different from $R_2$ or $R_3$ is different from $R_4$, and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation include, for example, p-isobutylstyrene, 2-vinyl-6-methoxy-2-naphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described, for example, in U.S. Pat. Nos. 4,329,507, 5,360,938 and 5,491,266.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809, 4,148,830, 5,312,996, and 5,929,289. Non-limiting examples of suitable solvents include saturated hydrocarbons (alkanes), aromatic hydrocarbons, water, ethers, polyethers, alkylated polyethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. In general, with regard to the production of achiral (non-optically active) aldehydes, it is preferred to employ aldehyde compounds corresponding to the aldehyde products desired to be produced and/or higher boiling aldehyde liquid condensation by-products as the main organic solvents as is common in the art. Such aldehyde condensation by-products can also be preformed if desired and used accordingly. Illustrative preferred solvents employable in the production of aldehydes include ketones, e.g., acetone and methylethyl ketone, esters, e.g., ethyl acetate, di-2-ethylhexyl phthalate, 2,2,4-trimethyl-1,3-pentanediol monoisobutyrate, hydrocarbons, e.g., toluene, nitrohydrocarbons, e.g., nitrobenzene, ethers, e.g., tetrahydrofuran (THF), and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. No. 4,148,380 and U.S. Pat. No. 4,247,486. Indeed, while one may employ, if desired, any suitable solvent at the start-up of a continuous process, the primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of two or more solvents may also be employed.

The catalyst useful in the hydroformylation process comprises a catalytic metal. The catalytic metal can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with preferred metals being rhodium, cobalt, iridium and ruthenium, more preferably rhodium, cobalt and ruthenium, especially rhodium.

The number of available coordination sites on such metals is well known in the art. Thus the catalytic species, which may comprise a complex catalyst mixture, may comprise monomeric, dimeric or higher nuclearity forms, which are preferably characterized by at least one organophosphite-containing molecule complexed per one molecule of metal, e.g., rhodium. For instance, it is considered that the catalytic species of the preferred catalyst employed in a hydroformylation reaction may be complexed with carbon monoxide and hydrogen in addition to the organophosphorus ligands in view of the carbon monoxide and hydrogen gas employed by the hydroformylation reaction.

Illustrative metal-organophosphorous ligand complexes employable in such hydroformylation reactions encompassed by this invention include the metal-organophosphorous ligand complex catalysts. The catalysts, as well as methods for their preparation, are well known in the art and include those disclosed in the above-mentioned patents. In general, such catalysts may be preformed or formed in situ as described in such references and consist essentially of metal in complex combination with an organophosphorous ligand. It is believed that carbon monoxide is also present and complexed with the metal in the active species. The active species may also contain hydrogen directly bonded to the metal. The metal-organophosphorous ligand complex catalyst can be optically active or non-optically active.

The permissible organophosphorous ligands that make up the metal-organophosphorous ligand complexes and free organophosphorous ligand include triarylphosphines, mono-, di-, tri- and higher polyorganophosphites. Mixtures of such ligands may be employed if desired in the metal-organophosphorous ligand complex catalyst and/or free ligand and such mixtures may be the same or different. This invention is not intended to be limited in any manner by the permissible organophosphorous ligands or mixtures thereof. It is to be noted that the successful practice of this invention does not depend and is not predicated on the exact structure of the metal-organophosphorous ligand complex species, which may be present in their mononuclear, dinuclear and/or higher nuclearity forms. Indeed, the exact structure is not known. While not intending to be bound to any theory or mechanistic discourse, it appears that the catalytic species may in its simplest form consist essentially of the metal in complex combination with the organophosphorous ligand and carbon monoxide and/or hydrogen.

The term "complex" as used herein and in the claims means a coordination compound formed by the union of one or more electronically rich molecules or atoms capable of independent existence with one or more electronically poor molecules or atoms, each of which is also capable of independent existence. For example, the organophosphorous ligands employable herein may possess one or more phosphorus donor atoms, each having one available or unshared pair of electrons that are each capable of forming a coordinate bond independently or possibly in concert, e.g., via chelation, with the metal. Among the organophosphorous ligands that may serve as the ligand of the metal-organophosphorous ligand complex catalyst are fluorophosphites, phosphinites, phosphino-phosphoramidites, monoorganophosphite, diorganophosphite, triorganophosphite, organopolyphosphite, phosphoramidites, organomonophosphoramidite and organopolyphosphoramidite compounds. Such organophosphorous ligands and/or methods for their preparation are well known in the art. Mixtures of the above ligands can also be used. Carbon monoxide, which is also properly classified as a ligand, can also be present and complexed with the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$, wherein each R is the same or different and is a substituted or unsubstituted hydrocarbon radical, e.g., the alkyl or aryl, acetate, acetylacetonate, $SO_4$, $PF_4$, $PF_6$, $NO_2$, $NO_3$, $CH_3$, $CH_2=CHCH_2$, $CH_3CH=CHCH_2$, $C_6H_5CN$, $CH_3CN$, $NH_3$, pyridine, $(C_2H_5)_3N$, mono-olefins, diolefins and triolefins, tetrahydrofuran, and the like. It is to be understood that the complex species are preferably free of any additional organic ligand or anion that might poison the catalyst or have an undue adverse effect on catalyst performance. It is preferred in the metal-organophosphite ligand complex catalyzed hydroformylation reactions that the active catalysts be free of halogen and sulfur directly bonded to the metal, although such may not be absolutely necessary.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Representative monoorganophosphites may include those having the formula:

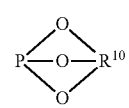

<<I>> wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306.

Representative diorganophosphites may include those having the formula:

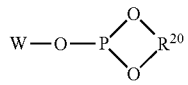

wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302 and the like. Illustrative divalent aromatic radicals include, for example, arylene, bisarylene, arylene-alkylene, arylene-alkylene-arylene, arylene-oxy-arylene, arylene-$NR^{24}$-arylene wherein $R^{24}$ is as defined above, arylene-S-arylene, and arylene-S-alkylene, and the like. More preferably $R^{20}$ is a divalent aromatic radical such as disclosed more fully, for example, in U.S. Pat. Nos. 4,599,206, 4,717,775, 4,835,299, and the like.

Representative of a more preferred class of diorganophosphites are those of the formula:

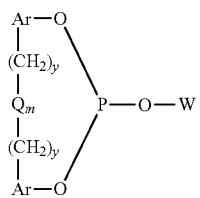

wherein W is as defined above, each Ar is the same or different and represents a substituted or unsubstituted aryl radical, each y is the same or different and is a value of 0 or 1, Q represents a divalent bridging group selected from —C($R^{33}$)$_2$—, —O—, —S—, —$NR^{24}$—, Si($R^{35}$)$_2$ and —CO—, wherein each $R^{33}$ is the same or different and represents hydrogen, an alkyl radical having from 1 to 12 carbon atoms, phenyl, tolyl, and anisyl, $R^{24}$ is as defined above, each $R^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835,299.

Representative triorganophosphites may include those having the formula:

wherein each $R^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Such triorganophosphites are described in greater detail, for example, in U.S. Pat. Nos. 3,527,809 and 5,277,532.

Representative organopolyphosphites contain two or more tertiary (trivalent) phosphorus atoms and may include those having the formula:

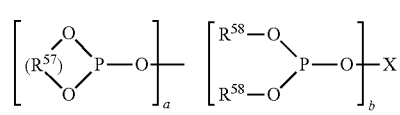

wherein X represents a substituted or unsubstituted n-valent organic bridging radical containing from 2 to 40 carbon atoms, each $R^{57}$ is the same or different and represents a divalent organic radical containing from 4 to 40 carbon atoms, each $R^{58}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. It is to be understood that when a has a value of 2 or more, each $R^{57}$ radical may be the same or different. Each $R^{58}$ radical may also be the same or different in any given compound.

Representative n-valent (preferably divalent) organic bridging radicals represented by X and representative divalent organic radicals represented by $R^{57}$ above, include both acyclic radicals and aromatic radicals, such as alkylene, alkylene-$Q_m$-alkylene, cycloalkylene, arylene, bisarylene, arylene-alkylene, and arylene-(CH$_2$)$_y$-$Q_m$-(CH$_2$)$_y$-arylene radicals, and the like, wherein each Q, y and m are as defined above in Formula (III). The more preferred acyclic radicals represented by X and $R^{57}$ above are divalent alkylene radicals, while the more preferred aromatic radicals represented by X and $R^{57}$ above are divalent arylene and bisarylene radicals, such as disclosed more fully, for example, in U.S. Pat. Nos. 4,769,498, 4,774,361, 4,885,401, 5,179,055, 5,113,022, 5,202,297, 5,235,113, 5,264,616 and 5,364,950, and 5,527,950. Representative preferred monovalent hydrocarbon radicals represented by each $R^{58}$ radical above include alkyl and aromatic radicals.

Illustrative preferred organopolyphosphites may include bisphosphites such as those of Formulas (VI) to (VIII) below:

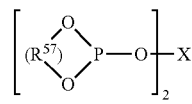

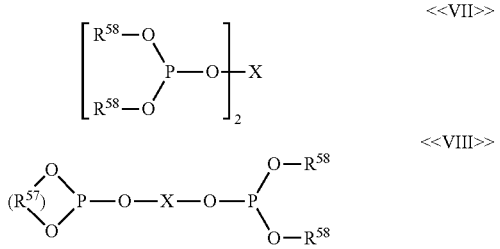

wherein each $R^{57}$, $R^{58}$ and X of Formulas (VI) to (VIII) are the same as defined above for Formula (V). Preferably each $R^{57}$ and X represents a divalent hydrocarbon radical selected from alkylene, arylene, arylene-alkylene-arylene, and bisarylene, while each $R^{58}$ radical represents a monovalent hydrocarbon radical selected from alkyl and aryl radicals. Organophosphite ligands of such Formulas (V) to (VIII) may be found disclosed, for example, in U.S. Pat. Nos. 4,668,651, 4,748,261, 4,769,498, 4,774,361, 4,885,401, 5,113,022, 5,179,055, 5,202,297, 5,235,113, 5,254,741, 5,264,616, 5,312,996, 5,364,950, and 5,391,801.

$R^{10}$, $R^{20}$, $R^{46}$, $R^{57}$, $R^{58}$, Ar, Q, X, m, and y in Formulas (VI) to (VIII) are as defined above. Most preferably X represents a divalent aryl-$(CH_2)_y$-$(Q)_m$-$(CH_2)_y$-aryl radical wherein each y individually has a value of 0 or 1; m has a value of 0 or 1 and Q is —O—, —S— or —C($R^{35})_2$— where each $R^{35}$ is the same or different and represents hydrogen or a methyl radical. More preferably each alkyl radical of the above defined $R^8$ groups may contain from 1 to 24 carbon atoms and each aryl radical of the above-defined Ar, X, $R^{57}$ and $R^{58}$ groups of the above Formulas (VI) to (VII) may contain from 6 to 18 carbon atoms and said radicals may be the same or different, while the preferred alkylene radicals of X may contain from 2 to 18 carbon atoms and the preferred alkylene radicals of $R^{57}$ may contain from 5 to 18 carbon atoms. In addition, preferably the divalent Ar radicals and divalent aryl radicals of X of the above formulas are phenylene radicals in which the bridging group represented by —$(CH_2)_y$-$(Q)_m$-$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Any of the $R^{10}$, $R^{20}$, $R^{57}$, $R^{58}$, W, X, Q and Ar radicals of such organophosphites of Formulas (I) to (VIII) above may be substituted if desired, with any suitable substituent containing from 1 to 30 carbon atoms that does not unduly adversely affect the desired result of the process of this invention. Substituents that may be on said radicals in addition to corresponding hydrocarbon radicals such as alkyl, aryl, aralkyl, alkaryl and cyclohexyl substituents, may include for example silyl radicals such as —Si($R^{35})_3$; amino radicals such as —N($R^{15})_2$; phosphine radicals such as -aryl-P($R^{15})_2$; acyl radicals such as —C(O)$R^{15}$ acyloxy radicals such as —OC(O)$R^{15}$; amido radicals such as —CON($R^{15})_2$ and —N($R^{15}$)COR$^{15}$; sulfonyl radicals such as —SO$_2$R$^{15}$, alkoxy radicals such as —OR$^{15}$; sulfinyl radicals such as —SOR$^{15}$, phosphonyl radicals such as —P(O)($R^{15})_2$, as well as halo, nitro, cyano, trifluoromethyl, hydroxy radicals, and the like, wherein each $R^{15}$ radical individually represents the same or different monovalent hydrocarbon radical having from 1 to 18 carbon atoms, e.g., alkyl, aryl, aralkyl, alkaryl and cyclohexyl radicals, with the proviso that in amino substituents such as —N($R^{15})_2$ each $R^{15}$ taken together can also represent a divalent bridging group that forms a heterocyclic radical with the nitrogen atom, and in amido substituents such as —C(O)N($R^{15})_2$ and —N($R^{15}$)COR$^{15}$ each $R^{15}$ bonded to N can also be hydrogen. It is to be understood that any of the substituted or unsubstituted hydrocarbon radicals groups that make up a particular given organophosphite may be the same or different.

As a further option, any organomonophosphoramidite or organopolyphosphoramidite ligand can be used as the, or in combination with any other, organophosphorous ligand. Organophosphoramidite ligands are known, and they are used in the same manner as organophosphite ligands. Representative organophosphoramidite ligands are of formulae IX-XI.

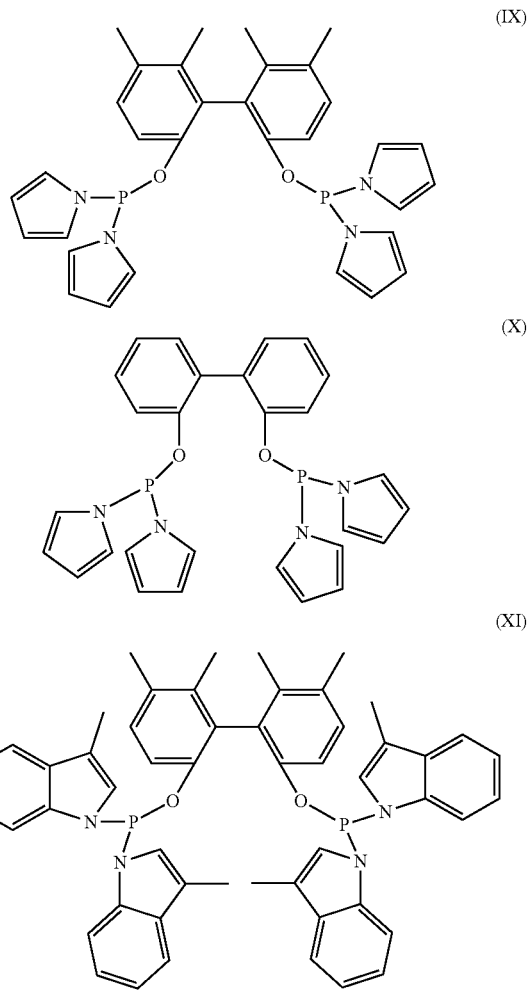

Organophosphoramidites are further described in, for example, U.S. Pat. No. 7,615,645.

The triarylphosphine employable in the process of this disclosure comprises any organic compound comprising at least one phosphorus atom covalently bonded to three aryl or arylalkyl radicals, or combinations thereof. A mixture of triarylphosphine ligands may also be employed. Representative organomonophosphines include those having the formula:

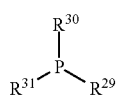

(XII)

wherein each $R^{29}$, $R^{30}$ and $R^{31}$ may be the same or different and represent a substituted or unsubstituted aryl radical containing from 4 to 40 carbon atoms or greater. Such triarylphosphines may be found described in greater detail, for example, in U.S. Pat. No. 3,527,809, the disclosure of which is incorporated herein by reference. Illustrative triarylphosphine ligands are triphenylphosphine, trinaphthylphine, tritolylphosphine, tri(p-biphenyl)phosphine, tri(p-methoxyphenyl) phosphine, tri(m-chlorophenyl)-phosphine, p-N,N-dimethylaminophenyl bis-phenyl phosphine, and the like. Triphenyl phosphine, i.e., the compound of Formula I wherein each $R^{29}$, $R^{30}$ and $R^{31}$ is phenyl, is an example of a preferred organomonophosphine ligand. The hydroformylation reaction is preferentially effected in a liquid body containing excess, free triarylphosphine.

Another preferred class of ligands suitable for this invention is polydentate ligands such as described in WO 2007/078859, U.S. Pat. No. 4,694,109, and U.S. Pat. No. 5,332,846.

As noted above, the metal-organophosphorous ligand complex catalysts may be formed by methods known in the art. The metal-organophosphorous ligand complex catalysts may be in homogeneous or heterogeneous form. For instance, preformed rhodium hydrido-carbonyl-organophosphorous ligand catalysts may be prepared and introduced into the reaction mixture of a hydroformylation process. More preferably, the rhodium-organophosphorous ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$, and the like may be introduced into the reaction mixture along with the organophosphorous ligand for the in situ formation of the active catalyst. In a preferred embodiment of this invention, rhodium dicarbonyl acetylacetonate is employed as a rhodium precursor and reacted in the presence of a solvent with the organophosphorous ligand to form a catalytic rhodium-organophosphorous ligand complex precursor that is introduced into the reactor along with excess (free) organophosphorous ligand for the in situ formation of the active catalyst. In any event, it is sufficient for the purposes of this invention that carbon monoxide, hydrogen and organophosphorous ligand compound are all ligands that are capable of being complexed with the metal and that an active metal-organophosphorous ligand catalyst is present in the reaction mixture under the conditions used in the hydroformylation reaction. Carbonyl and organophosphorous ligands, if not already complexed with the initial rhodium, may be complexed to the rhodium either prior to or in situ during the hydroformylation process.

By way of illustration, the preferred catalyst precursor composition consists essentially of a solubilized rhodium carbonyl organophosphite ligand complex precursor, a solvent and, optionally, free organophosphite ligand. The preferred catalyst precursor composition can be prepared by forming a solution of rhodium dicarbonyl acetylacetonate, an organic solvent and a organophosphite ligand. The organophosphite ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphite ligand complex precursor are soluble can be employed. The amounts of rhodium complex catalyst precursor, organic solvent and organophosphite ligand, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or organophosphite ligand, to form the active complex catalyst as explained above. The acetylacetone that is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor and hydroformylation start-up.

Accordingly, the metal-organophosphite ligand complex catalyst used in the process of this invention consists essentially of the metal complexed with carbon monoxide and a organophosphite ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the organophosphite ligand. Further, such terminology does not exclude the possibility of other organic ligands and/or anions that might also be complexed with the metal. Materials in amounts that unduly adversely poison or unduly deactivate the catalyst are not desirable and so the catalyst most desirably is free of contaminants such as metal-bound halogen, e.g., chlorine, and the like, although such may not be absolutely necessary. The hydrogen and/or carbonyl ligands of an active metal-organophosphite ligand complex catalyst may be present as a result of being ligands bound to a precursor catalyst and/or as a result of in situ formation, e.g., due to the hydrogen and carbon monoxide gases employed in hydroformylation process.

As noted, the hydroformylation process of this invention involves the use of a metal-organophosphorous ligand complex catalyst as described herein. Mixtures of such catalysts can also be employed if desired. The amount of metal-organophosphorous ligand complex catalyst present in the reaction fluid of a given hydroformylation process encompassed by this invention need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal.

In addition to the metal-organophosphorous ligand complex catalyst, free organophosphorous ligand, i.e., ligand that is not complexed with the metal, may also be present in the reaction medium. The free organophosphorous ligand may correspond to any of the above-defined organophosphorous ligands discussed above as employable herein. It is preferred that the free organophosphorous ligand be the same as the organophosphorous ligand of the metal-organophosphorous ligand complex catalyst employed. However, such ligands need not be the same in any given process. The hydroformylation process may involve from 0.1 moles or less to 100 moles or higher of free organophosphorous ligand per mole of metal in the reaction medium. Preferably, the hydroformylation process is carried out in the presence of from 1 to 50 moles of organophosphorous ligand per mole of metal present in the reaction medium. More preferably, for organopolyphosphites, from 1.1 to 4 moles of organopolyphosphite ligand are employed per mole of metal. Said amounts of organophosphorous ligand are the sum of both the amount of organophosphorous ligand that is bound (complexed) to the metal present and the amount of free (non-complexed) organophosphorous ligand present. Since it is more preferred to produce non-optically active aldehydes by hydroformylating achiral olefins, the more preferred organophosphorous ligands are achiral type organophosphorous ligands, especially those encompassed by Formula (V) above, and more preferably those of Formulas (VI), (VII) and (VIII) above. If desired, make-up or additional organophosphorous ligand can be supplied to the reaction medium of the hydroformylation process at any time and in any suitable manner, e.g., to maintain a predetermined level of free ligand in the reaction medium.

As indicated above, the hydroformylation catalyst may be in heterogeneous form during the reaction and/or during the product separation. Such catalysts are particularly advantageous in the hydroformylation of olefins to produce high boiling or thermally sensitive aldehydes, so that the catalyst may be separated from the products by filtration or decantation at low temperatures. For example, the rhodium catalyst may be attached to a support so that the catalyst retains its solid form during both the hydroformylation and separation stages, or is soluble in a liquid reaction medium at high temperatures and then is precipitated on cooling.

The use of an aqueous extraction system, preferably employing a buffer solution, to prevent and/or lessen hydrolytic degradation of an organophosphite ligand and deactivation of a metal-organophosphite ligand complex is well known and is disclosed, e.g., in U.S. Pat. No. 5,741,942 and U.S. Pat. No. 5,741,944. Such buffer systems and/or methods for their preparation are well known in the art. Mixtures of buffers may be employed.

Illustrative metal-organophosphorous ligand complex catalyzed hydroformylation processes that may experience hydrolytic degradation include those processes as described, for example, in U.S. Pat. Nos. 4,148,830, 4,593,127, 4,769, 498, 4,717,775, 4,774,361, 4,885,401, 5,264,616, 5,288,918, 5,360,938, 5,364,950, 5,491,266 and 7,196,230. P—Z containing species that will likely undergo hydrolytic degradation include organophosphonites, phosphoramidites, fluorophosphonites, and the like such as described WO 2008/071508, WO 2005/042458, and U.S. Pat. Nos. 5,710,344, 6,265,620, 6,440,891, 7,009,068, 7,145,042, 7,586,010, 7,674,937, and 7,872,156. These species will generate a variety of acidic and/or polar degradation products that can be removed by use of technology disclosed in U.S. Pat. Nos. 5,744,649 and 5,741,944. Accordingly, the hydroformylation processing techniques that are advantageously employed with the invention disclosed herein may correspond to any known processing techniques. Preferred hydroformylation processes are those involving catalyst liquid recycle.

Extraction contacting conditions may vary greatly and any suitable combination of such conditions may be employed herein. For instance, a decrease in one of such conditions may be compensated for by an increase in one or more of the other conditions, while the corollary is also true. In general, liquid temperatures ranging from 10° C. to 120° C., preferably from 20° C. to 80° C., and more preferably from 25° C. to 60° C., should be suitable for most instances, although lower or higher temperatures may be employed if desired. Advantageously, the treatment is carried out at pressures ranging from ambient to reaction pressure, and the contact time may vary from a matter of seconds or minutes to a few hours or more.

Success in removing phosphorus acidic compounds from the reaction fluid may be determined by measuring the rate of degradation (consumption) of the organophosphorous ligand present in the hydroformylation reaction medium. The consumption rate can vary over a wide range, e.g., from <0.6 up to 5 grams per liter per day, and will be governed by the best compromise between cost of ligand and treatment frequency to keep hydrolysis below autocatalytic levels. Preferably, the aqueous buffer solution treatment is carried out in such a manner that the consumption of the desired organophosphorous ligand present in the hydroformylation reaction medium is maintained at an acceptable rate, e.g., <0.5 grams of ligand per liter per day, and more preferably <0.1 grams of ligand per liter per day, and most preferably <0.06 grams of ligand per liter per day. As the neutralization and extraction of phosphorus acidic compounds into the aqueous buffer solution proceeds, the pH of the buffer solution will slowly decrease.

The removal of at least some amount of phosphorus acidic compounds, for example, $H_3PO_3$, $H_3PO_4$, aldehyde acids such as hydroxy alkyl phosphonic acids, such as hydroxyl butyl phosphonic acid and hydroxyl pentyl phosphonic acid, and the like, from the hydroformylation system allows one to control the acidity of the hydroformylation reaction medium, thereby stabilizing the useful organophosphorous ligand by preventing or lessening its hydrolytic decomposition.

A slow loss in catalytic activity has been observed when organopolyphosphite ligand promoted metal catalysts are employed in processes that involve harsh conditions such as recovery of the aldehyde via vaporization.

Optionally, an organic nitrogen compound may be added to the hydroformylation reaction fluid to scavenge the acidic hydrolysis by-products formed upon hydrolysis of the organophosphorous ligand, as taught, for example, in U.S. Pat. No. 4,567,306. Such organic nitrogen compounds may be used to react with and to neutralize the acidic compounds by forming conversion product salts therewith, thereby preventing the catalytic metal from complexing with the acidic hydrolysis by-products and thus helping to protect the activity of the catalyst while it is present in the reaction zone under reaction conditions.

Preferred organic nitrogen compounds useful for scavenging the phosphorus acidic compounds are heterocyclic compounds selected from the group consisting of diazoles, triazoles, diazines and triazines, and the like, such as those disclosed in U.S. Pat. No. 5,731,472. Benzimidazole and benztriazole are preferred. The amount of organic nitrogen compound that may be present in the reaction fluid is typically sufficient to provide a concentration of at least 0.0001 moles of free organic nitrogen compound per liter of reaction fluid. In general, the ratio of organic nitrogen compound to total organophosphorous ligand, whether bound or present as free organophosphorous ligand, is at least 0.1:1 and even more preferably at least 0.5:1. Organic nitrogen compound:organophosphorous ligand molar ratios of from 1:1 to 5:1 should be sufficient for most purposes.

The aqueous buffer solution treatment will not only remove free phosphoric acidic compounds from the metal-organophosphorous ligand complex catalyst containing reaction fluids, but it also removes the phosphorus acidic material of the conversion product salt formed by the use of the organic nitrogen compound scavenger when employed, i.e., the phosphorus acid of said conversion product salt remains behind in the aqueous buffer solution, while the treated reaction fluid, along with the reactivated (free) organic nitrogen compound is returned to the reaction zone.

When using hydrolyzable ligands, it is preferred to employ means to remove ligand degradation products from the process to avoid acid-catalyzed autocatalytic ligand degradation. The use of extractors, amine additives, epoxides and other means are known for control and/or removal of these degradation products. See, e.g., U.S. Pat. No. 5,741,942, U.S. Pat. No. 5,741,944, JP 3864668, U.S. Pat. No. 5,648,554, U.S. Pat. No. 5,731,473, U.S. Pat. No. 5,744,649, U.S. Pat. No. 5,789,625, U.S. Pat. No. 6,846,960, and U.S. Pat. No. 6,995,292. These degradation product control means are advantageously implemented on the catalyst recycle stream, and can be located before or after the recycle stream is split following the vaporizer.

The process of the invention employs at least 2 reactor trains, each of which has its own olefin feed stream to the first reaction zone of the train, and each feed stream can be identical to or different from the other. For the purposes of the invention, the term "reactor train" means an equipment system comprising at least one reactor that feeds at least a portion of the liquid effluent to a product-catalyst separation zone. A reactor train can have multiple reactors arranged in parallel, series, or both. In one embodiment of the invention, the process employs 2 reactor trains. Preferably, the trains are operated in parallel, although other modes of operation are possible. For the sake of brevity, the process as described hereinafter will refer to a system with two reactor trains. The term "first reactor" refers to the first reactor in the first reactor train. The term "in parallel" is intended to include configurations such as those shown in FIGS. 5, 6, and 8.

Each reactor vessel may comprise a single reaction zone or multiple reaction zones, such as, for example, described in U.S. Pat. No. 5,728,893. In various embodiments of the invention, two or three reaction zones are present in a single reactor vessel.

Each olefin feed stream is subjected to hydroformylation in its respective train. The first reactor train is characterized by having a higher reactivity olefin feed either by structure, e.g., ethylene>propylene>1-olefins>2-olefins, or concentration, inerts giving lower reactivity. "Reactivity" can be defined as kg-mols product/hr/kg-mol rhodium or kJ/hr/liter reactor volume. Highly reactive feeds that generate substantial heat of reaction must be controlled more rigorously than less reactive feeds.

Within a reactor train or reactor, reaction zones can be arranged in series or in parallel. The hydroformylation process may be conducted in an elongated tubular zone or series of such zones.

Examples of single train hydroformylation designs are disclosed in EP 1 008 580, U.S. Pat. No. 5,105,018, U.S. Pat. No. 7,615,645, U.S. Pat. No. 7,329,783, and CN 101293818. In one embodiment, the hydroformylation process may be carried out in a multi-zone or multistaged reactor such as described, for example, in U.S. Pat. No. 5,728,893. Such multistaged reactors can be designed with internal, physical barriers that create more than one reaction zone or theoretical reactive stage per vessel. In effect, a number of reactor zones are contained inside a single continuous stirred tank reactor vessel. Putting multiple reaction zones in a single vessel is a cost effective way of using reactor vessel volume, and significantly reduces the number of vessels that otherwise would be required to achieve the same results. Having fewer vessels reduces the overall capital required and reduces maintenance concerns associated with having separate vessels and agitators.

The hydroformylation process may be carried out using one or more suitable reactor types such as, for example, a tubular reactor, a bubble column reactor, or a continuous stirred tank reactor (CSTR). A reaction zone may be fitted with one or more internal and/or external heat exchanger(s) in order to control temperature fluctuations, and to prevent any possible "runaway" reaction temperatures.

The choice of suitable materials of construction for process equipment can be readily made by those skilled in the art. The materials employed should be substantially inert to the starting materials and the reaction mixture, and the process equipment should be able to withstand the reaction temperatures and pressures. For example, the hydroformylation process may be conducted in either glass lined, stainless steel or similar type reaction equipment.

Means to introduce and/or adjust the quantity of starting materials or ingredients introduced batchwise, semi-continuously or continuously into the reaction zone during the course of the reaction can be conveniently utilized in the process, and such means are useful to maintain the desired molar ratio of the starting materials. The reaction steps may be effected by the incremental addition of one of the starting materials to the other.

The hydroformylation process of the invention may be conducted in one or more zones or stages within each train. As is known to those skilled in the art, the exact configuration of the reaction trains, including the number of reaction zones or stages, will be governed by the best compromise between capital costs and achieving high catalyst selectivity, activity, lifetime and ease of operability, as well as the intrinsic reactivity of the starting materials in question, the stability of the starting materials and the desired reaction product(s) to the reaction conditions within each train.

Figure 5:
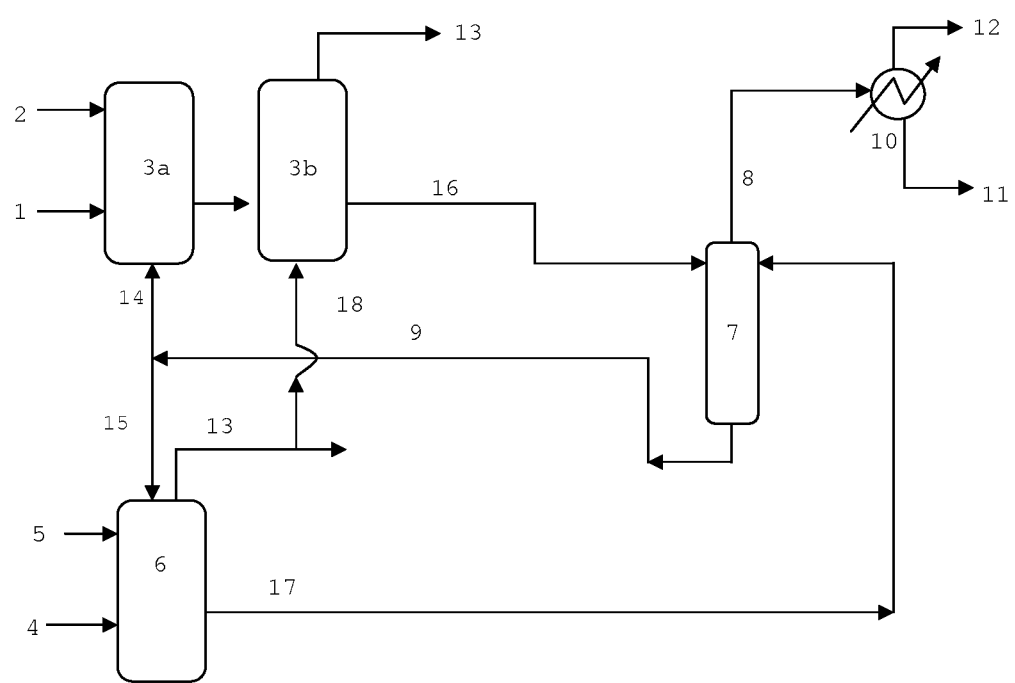
FIG. 5 is a schematic of an hydroformylation process that employs a common product-catalyst separation zone, e.g., a thin film vaporizer.
Figure 6:
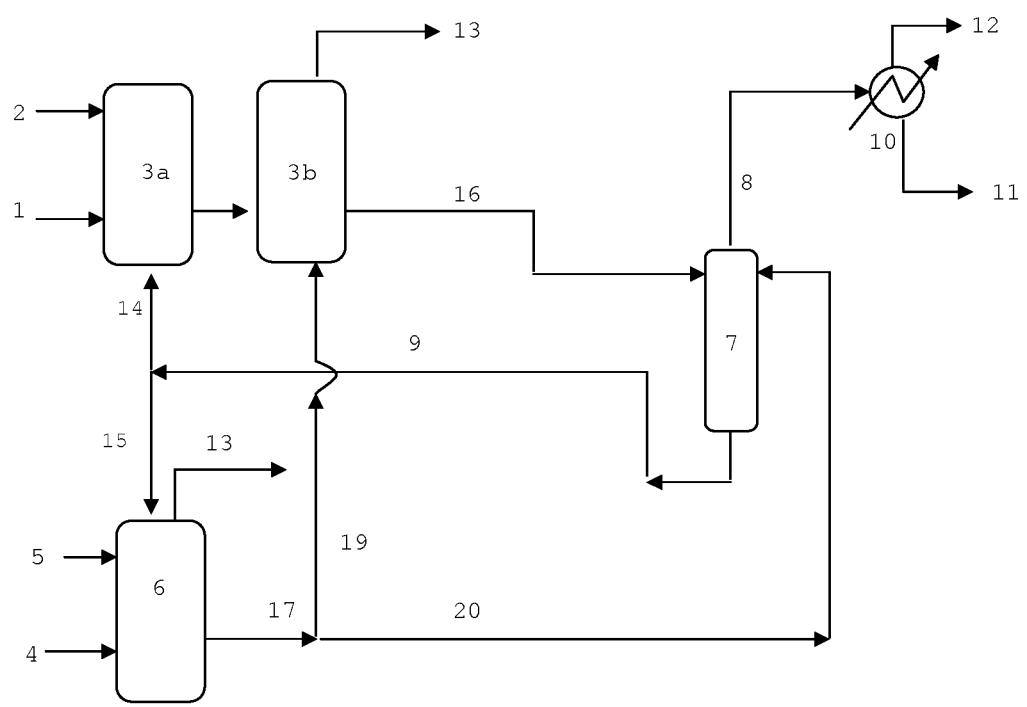
FIG. 6 is a schematic of an hydroformylation process that employs a common product-catalyst separation zone, e.g., a thin film vaporizer.
Figure 8:
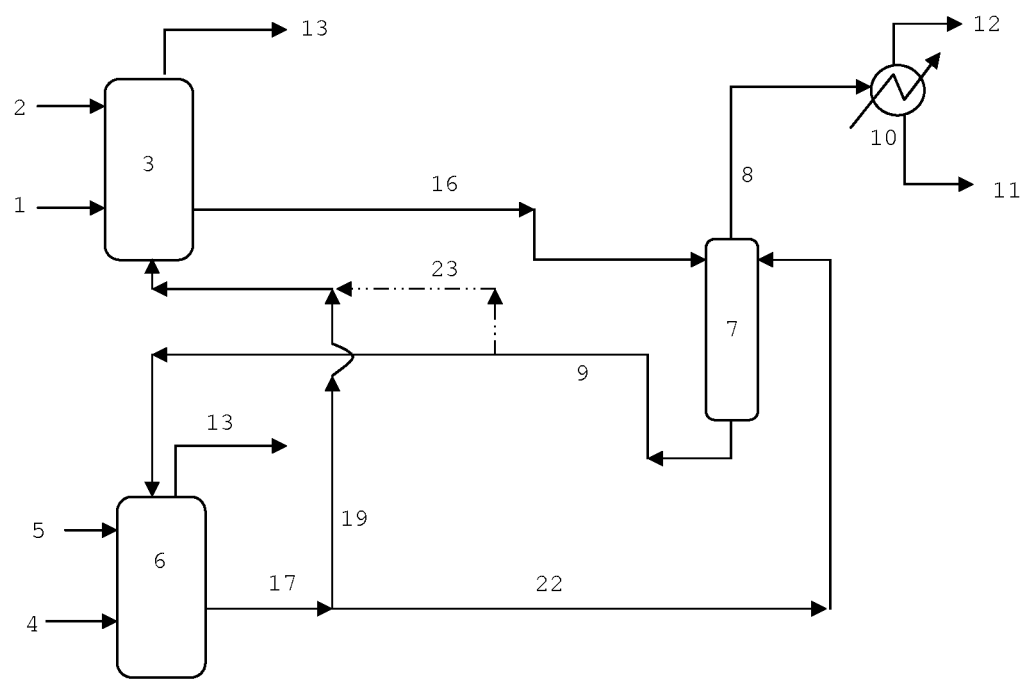
FIG. 8 is a schematic of an hydroformylation process that employs a common product-catalyst separation zone, e.g., a thin film vaporizer.

In one embodiment, one or more effluent streams from one train are fed to the other reactor train. For example, an effluent stream from the additional reactor train can be added to the second reaction zone of the first reactor train such that the majority of the reaction in both trains has already occurred. The need for rigorous control of reaction temperature and N:I ratio following the first reaction zone is less critical, and improved conversion of the small amount of remaining olefin(s) is of primary interest. In effect, this configuration employs a reaction zone after the first reaction zone as a "polishing" reaction zone for the other reactor train. In this flow scheme, the common product-catalyst separation zone is processing the output of both trains, even though the effluent of the trains merge to some extent within one of the trains upstream of the product-catalyst separation zone. Embodiments of this configuration are shown in FIGS. 5, 6, and 8.

In one embodiment of the invention, the catalytic metal concentration in the first reactor is determined indirectly according to methods well known to those skilled in the art. For example, the relative concentration of aldehyde heavies, ligands, ligand decomposition products (oxides, etc.), or other markers, which correlate to the rhodium, can be analyzed by gas chromatography, high pressure liquid chromatography (HPLC), UV-Vis or IR spectrosocopy and other well-known techniques. If the catalytic metal concentration is too high or too low, the fraction of the total catalyst recycle mass from the vaporizer can be lowered or raised, respectively, in order to effect the desired change to the catalytic metal concentration in the first reactor train.

The concentration of catalytic metal in the first reactor can be correlated to the mass ratio of (a) fresh olefin fed to the first reactor to (b) the total amount of fresh olefin fed to all reactor trains. Based on this ratio, the metal concentration in the first reactor is controlled by changing the mass ratio of catalyst recycle streams fed to the reactor trains. The relevant flow rates can be measured using mass flow meters. Alternatively, the mass ratio of the catalyst recycle streams may be measured directly.

Ethylene and propylene hydroformylation reaction kinetics are more responsive to changes in the kinetic variables than the kinetics for higher olefins. Thus, one preferred control scheme will control the catalytic metal concentration of the first reactor train and will allow the catalytic metal concentration in the second reaction train to vary or "float." The temperature of the second reactor train, which can be controlled via means known to those skilled in the art, can be reduced to offset any effects of higher than design catalytic metal concentrations in the second reactor train, if desired.

The concentration of catalytic metal in a reactor can be controlled by monitoring the olefin partial pressure in the reactor. For a given temperature and CO partial pressure, the olefin partial pressure generally is a function of catalytic metal content; thus, if olefin partial pressure is out of the desired range, then the catalyst recycle flow can be adjusted to keep the olefin partial pressure within the desired range based on known kinetics for the catalyst. This "inferential control" can employ commercially available monitoring systems.

In one embodiment, for added temperature control, especially in the first reactor, it is preferred to keep the $H_2$ partial pressure considerably lower than stoichiometric requirements, such as described in U.S. Pat. No. 4,593,127. This will act as a inherent brake to stop a "run-away" reaction since the supply of $H_2$ would be quickly exhausted and the reaction would stop. The needed $H_2$ can be added to downstream reactors where the potential for run-away reactions is lower since there is less olefin available to react.

The hydroformylation products may be asymmetric, non-asymmetric or a combination thereof, with the preferred products being non-asymmetric. The process may be conducted in any batch, continuous or semi-continuous fashion and may involve any catalyst liquid recycle operation desired. It is generally preferred to carry out the hydroformylation process in a continuous manner. Continuous hydroformylation processes are well known in the art.

The reaction conditions of the hydroformylation process within each reactor train may include any suitable type hydroformylation conditions heretofore employed for producing optically active and/or non-optically active aldehydes. For instance, the total gas pressure of hydrogen, carbon monoxide and olefin starting compound of the hydroformylation process may range from 100 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominantly by the amount of reactants necessary to obtain a desired rate of reaction. More specifically the carbon monoxide partial pressure of the hydroformy-lation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, $H_2$:CO molar ratio of gaseous hydrogen to carbon monoxide in a reaction zone may range from 1:10 to 100:1 or higher, the more preferred hydrogen to carbon monoxide molar ratio being from 1:10 to 10:1.

In general, the hydroformylation process may be conducted at any operable reaction temperature. Advantageously, the hydroformylation process is conducted at a reaction temperature of from −25° C. to 200° C. In general, hydroformylation reaction temperatures of 50° C. to 120° C. are preferred for all types of olefinic starting materials. As is known to those skilled in the art, the hydroformylation reaction conditions employed are governed by the type of aldehyde product desired.

It is well known that the product N:I ratio of linear and branched aldehyde isomers is dependent on a number of factors including ligand identity and concentration, usually defined as the ligand-to-rhodium ratio, temperature, and CO and $H_2$ partial pressures. Known methods for controlling the N:I ratio may be employed in the process of the invention. For example, each train can have different Rh concentrations, CO and $H_2$ partial pressures, and temperatures. In the event both trains employ the same olefin, or two olefins of nearly equal reactivity, variation in these parameters may allow for variable product N:I as well.

In one embodiment, the temperature and CO and $H_2$ partial pressures in the two trains can be the same or different to optimize conversion and N:I ratio for each olefin within each train. Additionally, the temperatures and partial pressures in different reactors within each train may be optimized separately depending on the optimal conditions for each olefin. Within each reactor train, the CO and $H_2$ partial pressures can be optimized and changed independently to adjust for changes in rhodium concentrations and residence times that may result in changes in the catalyst recycle rate and rhodium concentration. This allows for enhanced reactor stability and product N:I ratio control.

In one embodiment, one train may be run under "isomerizing conditions" as taught in U.S. Pat. No. 7,615,645. These conditions may be desirable for one olefin feed and not the other, depending on the desired product mix.

In yet another embodiment, as the feed rates to the separate trains change, the residence time in each train will change and thus the reactor temperature(s) within each train can be further optimized without impacting the other train. For example, if the feed supply to the first train is reduced, the residence time within the first reactor train will increase. If the conversion is already close to 100%, this longer residence time is not contributing to production but only contributes to higher ligand degradation and heavies formation. Therefore, the reactor temperatures can be reduced to reduce these losses without losing significant olefin conversion.

It is well known that the reaction rate is a function of temperature and catalyst concentration, among other factors. The rate of conversion is controlled primarily by controlling the temperature of the reaction mass and the concentration of the catalyst in each reactor train. In one embodiment, the flow rate of at least one of the catalyst recycle streams is controlled in order to control the concentration of catalyst in the first reactor train. In one embodiment of the invention, the control is effected by setting the desired catalytic metal concentration for the first reactor train. In one embodiment of the invention, the catalytic metal concentration in the first reactor is determined directly by analytical methods, which can be performed online or offline. Examples of direct analytical methods include inductively coupled plasma mass spectroscopy, atomic absorption spectrosocopy, HPLC and X-ray fluorescence.

At a given temperature, all else being equal, the hydroformylation reaction rate is directly proportional to the catalytic metal concentration. The catalytic metal concentration in each reactor train is related to the mass flow rate and catalytic metal concentration of each recycle stream. Thus, the hydroformylation reaction rate is a function of the recycle mass flow rate and the concentration of catalyst catalytic metal in the recycle stream.

The process of the invention employs a common product-catalyst separation zone, i.e., at least a portion of the effluent from each reactor train is sent, directly or indirectly, to a shared product-catalyst separation zone in which the effluent is separated into a stream comprising primarily product and a stream comprising the relative majority of the catalyst in solution, i.e., the catalyst recycle stream. The product stream advantageously is sent for further processing, e.g., refining. The catalyst recycle stream is recycled directly or indirectly back to the reactor trains. In one embodiment of the invention, the catalyst recycle stream exits the separation zone and is split directly between the reactor trains. For the purposes of the invention, the term "product-catalyst separation zone" means any means to separate a substantial portion of the aldehyde product from a mixture of product and catalyst solution. Advantageously, more than 90% and more preferably, more than 95% of the total product that is removed from the process is separated from the catalyst in the product-catalyst separation zone, although relatively small portions of product may also be collected by other equipment, such as vent knockout pots and the like.

One preferred and conventional method of product-catalyst separation is distillation, preferably in a falling-film evaporator, in one or more stages under normal, reduced or elevated pressure, as appropriate, with the non-volatilized metal catalyst-containing residue being recycled to the reactor trains. For example, separation and catalyst recycle for a single train is shown in U.S. Pat. No. 5,288,918, and the separation techniques employed there can be employed in the process of the invention.

Figure 7:
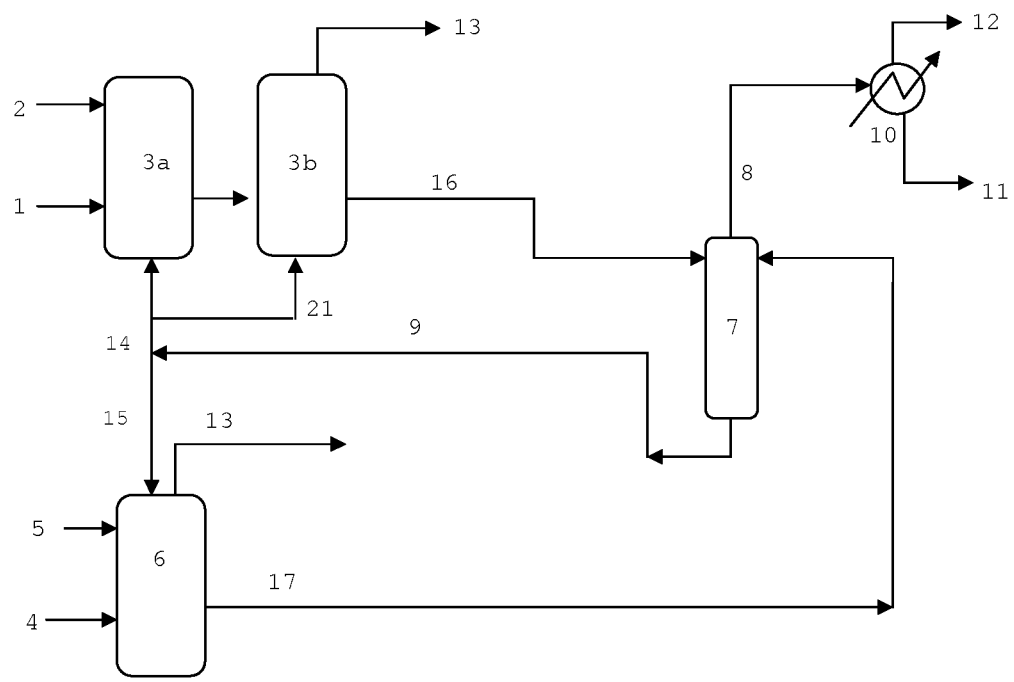
FIG. 7 is a schematic of an hydroformylation process that employs a common product-catalyst separation zone, e.g., a thin film vaporizer.

Preferably, the effluent of the first reactor train is fed directly or indirectly to a vaporizer. Similarly, in one embodiment of the invention, the effluent of the second reactor train, is fed directly, e.g., as shown in FIGS. 1, 5, and 7, or indirectly, e.g., as shown in FIGS. 6 and 8, to the same vaporizer. The non-vaporized, liquid effluent from the common vaporizer advantageously is split and recycled to the first and second reactor trains. The vapor effluent product stream from the vaporizer can be handled by conventional means such as, for example, sending it to a refining step.

The common vaporizer may comprise multiple vaporization units in series, such as high pressure and low pressure vaporizers, as shown, for example, in CN102826969. For example, each train may have its own high pressure vaporizer, and each non-volatilized stream from the high pressure vaporizers is fed to the common low pressure vaporizer. This allows recycling of pressurized lights, such as propylene or butene, to each train from the high pressure vaporizer, and the final product-catalyst separation is performed in the common low pressure vaporizer. In any case, the common final catalyst recycle stream is split, either at or after the vaporizer, and is sent back to the reactor trains.

As indicated above, the desired aldehydes may be recovered from the reaction mixture. For example, the recovery techniques disclosed in U.S. Pat. Nos. 4,166,773, 4,148,830 and 4,247,486 can be employed. In a continuous liquid catalyst recycle process, the portion of the liquid reaction mixture, containing aldehyde product, catalyst, etc., i.e., reaction fluid, removed from the reactor trains can be passed to a product-catalyst separation zone, e.g., vaporizer/separator, wherein the desired aldehyde product can be separated via distillation, in one or more stages, under normal, reduced or elevated pressure, from the liquid reaction fluid, then condensed and collected in a product receiver, and further refined or purified if desired. The remaining non-volatilized catalyst containing liquid reaction mixture may be recycled back to the reactor trains, as may any other volatile materials, e.g., unreacted olefin, together with any hydrogen and carbon monoxide after separation thereof from the condensed aldehyde product. In general, it is preferred to separate the desired aldehydes from the catalyst-containing reaction mixture under reduced pressure and at low temperatures so as to avoid possible degradation of the organophosphorous ligand and reaction products.

More particularly, distillation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. It is generally preferred that such aldehyde distillation take place under a total gas pressure that is lower than the total gas pressure employed during hydroformylation when low boiling aldehydes, e.g., $C_3$ to $C_6$, are involved, or under vacuum when high boiling aldehydes, e.g., $C_7$ or greater, are involved. In general, distillation pressures ranging from vacuum pressures up to a total gas pressure of 340 kPa (49.3 psia) are sufficient for most purposes.

A common practice is to degas the liquid reaction product medium removed from the hydroformylation reactor prior to the product-catalyst separation zone so as to volatilize a substantial portion of the unreacted gases dissolved in the liquid medium. These unreacted gases can be recycled, if desired.

One surprising benefit of using a common vaporizer, as compared to separate vaporizers, is that, in the case where the olefin in the first reactor train is lighter than the olefin of the other reactor trains, the presence of a high flow of the lighter components (from the first reactor train) will act to help "strip" the higher molecular weight components generated in the second train out of the vaporizer, particularly the aldol heavies formed as a natural side reaction. This allows vaporization to be carried out at a lower average temperature, thereby reducing potential heavies formation and ligand degradation. These heavies, which are described in U.S. Pat. No. 4,148,830, can build up over time and limit catalyst life. The vaporizer operating conditions, particularly temperature, preferably are controlled to avoid or minimize ligand degradation. Ligand degradation is discussed in detail in WO 2010/003073.

In one embodiment, the catalyst recycle stream sent to the each reaction train may be split between two or more different reactors within each train to control the N:I ratio within each train as taught in WO 2011/087690. This also reduces the average residence time of the catalyst at elevated temperature, thereby reducing heavies formation and ligand decomposition.

The recycle procedure generally involves withdrawing a portion of the liquid reaction medium containing the catalyst and aldehyde product from at least one of the hydroformylation reactor trains, either continuously or intermittently, and recovering the aldehyde product therefrom by use of a product-catalyst separation zone. Collection of the removed aldehyde product, typically by condensation of the volatilized materials, and separation and further refining thereof, e.g., by distillation, can be carried out in any conventional manner, and the crude aldehyde product can be passed on for further purification and isomer separation, if desired, and any recovered reactants, e.g., olefinic starting material and syngas, can be recycled in any desired manner to the hydroformylation zone (reactor). The aldehyde products can be refined by distillation, including multi-step distillation, to remove unreacted material and recover a purified product. Unreacted recovered reactants can optionally be concentrated for recycle to the reaction system either with or without subsequent processing. The recovered non-volatilized metal catalyst-containing residue of such separation can be recycled, to one or more of the hydroformylation reactor trains in any conventional manner desired.

Various types of recycle procedures are known in the art and may involve the liquid recycling of the metal-organophosphorous complex catalyst fluid separated from the desired aldehyde reaction product(s), such as disclosed, for example, in U.S. Pat. No. 4,148,830. A continuous liquid catalyst recycle process is preferred. Examples of suitable liquid catalyst recycle procedures are disclosed in U.S. Pat. Nos. 4,668,651, 4,774,361, 5,102,505 and 5,110,990.

The resulting product stream can be processed by conventional means. For example, the aldehyde products can be separated and separately processed by hydrogenation or aldolisation/hydrogenation to alcohols. Alternatively, the aldehyde products are not separated but are processed together. For example, the aldehyde mixture can be hydrogenated and the individual alcohols can be separated after hydrogenation. Another possibility involves aldolization/ hydrogenation to a mixture of alcohols and higher alcohols followed by distillation to isolate the individual alcohols. An example of such multiple processing schemes is given in WO 2012/008717.

The use of an extractor, mentioned above, may introduce various levels of water to the catalyst recycle streams and thereby, to the reactor trains. As taught in WO 2012/064586 and JP 2006/306815, the presence of water in the hydroformylation reactors may be important to mitigate reactor fouling. A primary source of this water is from the extractor, and a primary means to remove water is via a vaporizer. Changes in the catalyst recycle rate will necessarily change the amount of water being delivered to each train and it may be desirable to have auxiliary means to add water to each train independently. Alternatively, it may be desirable to keep one train "dry" to mitigate ligand hydrolysis, as taught in U.S. Pat. No. 7,262,330. Thus only treating one catalyst recycle stream may be desirable in order to remove the degradation acids from the more tolerant train. The extraction process, if employed, may comprise a single vessel or may comprise two or more discreet vessels.

The hydroformylation process of the invention can be conducted with recycle of unconsumed catalytic and non-catalytic starting materials if desired. When complete conversion is not desired or not obtainable, the starting materials can be separated from the product, for example by distillation, and the starting materials then recycled back to a reaction zone.

Illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, cyclohexane-dialdehyde, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g., S-2-(p-isobutylphenyl)-propionaldehyde, S-2-(6-methoxy-2-naphthyl)propionaldehyde, S-2-(3-benzoylphenyl)-propionaldehyde, S-2-(p-thienoylphenyl)propionaldehyde, S-2-(3-fluoro-4-phenyl)phenylpropionaldehyde, S-2-[4-(1,3-dihydro-1-oxo-2H-isoindol-2-yl)phenyl] propionaldehyde, and S-2-(2-methylacetaldehyde)-5-benzoylthiophene.

Various embodiments of the process are shown in FIGS. 1 and 5-8.

In FIG. 1, propylene (1) and syngas (2) are fed to the first train represented by reactor (3). $C_4$ Raffinate (4) and syngas (5) are fed to the second train represented by reactor (6). The effluent of reactors (3) and (4) are fed to product-catalyst separation zone (7) wherein a product (stream (8)) is separated from catalyst recycle (stream (9)). (Stream (8)) is condensed by condenser (10) to obtain mixed aldehydes (11) that are then separated by conventional means, such as distillation. The lights (12) may be purged or recycled as appropriate. Each reactor train may have optional vents (13), and portions of each vent may be recycled as desired. Recycle (stream (9)) comprising catalyst, excess ligand, solvent (usually aldehyde heavies), residual aldehyde products, and unreacted reactants is returned to the two reactor trains via (streams (14) and (15)).

Referring to FIG. 5, at least a portion of the vent (stream (13a)) from one or more reactors within one train can be fed to one or more of the reactors of the other train via line (18). Preferably, the vent (stream (18)) from the last reactor in the second train is sent to the first reactor train and, most preferably, to the last reactor (3b) of the first train. Vent line (13a) may have a knockout pot to collect condensable compounds, such as aldehyde products, and the non-condensed olefin and syngas are sent via line 18 to the other train.

Referring to FIG. 6, at least a portion of the liquid output (stream (17)) from one or more reactors from one train can be fed to one or more of the reactors of the other train via line (19). Preferably, the output from the last reactor (6) in the second train is sent to the first reactor train via line (19) and most preferably, to the last reactor of the first train. The resulting combined output (16) from the final reactor in the first train, which comprises output from both trains, is then sent to the common product-catalyst separation zone (7).

Line (20) may be used to balance flows or may be used if the first train is not available or if either train is running at reduced rates.

Referring to FIG. 7, a portion of the catalyst recycle (stream (14)) is divided between reactors within one train. A portion (stream (14)) is diverted via line (21) to a subsequent reactor (3b). In one embodiment of the invention, the rhodium concentration in either the first (3a) or subsequent (3b) reactors is controlled. Preferably, the rhodium concentration in the first reactor (3a) in the first train is controlled and is allowed to float in the downstream reactor (3b) in the first train. Preferably, the overall rhodium concentration in the final reactor (3b) in the first train is also monitored, e.g., at (stream (16)), to determine the (stream (14)) to (stream (15)) split ratio, i.e., the Catalyst Split Ratio. The flow rate of (stream (21)) may be used to control rhodium concentration within the reactors in the first train to control N:I ratio as taught in WO 2011/087690.

In FIG. 8, two trains are operated in a substantially parallel manner. The catalyst supply for the first train is at least partially supplied by a portion of the output from the second train (stream (19)) instead of exclusively from the separation zone. The catalyst recycle is substantially all sent to the second train via line (9). This scheme can be utilized when the rhodium requirement for the first train is substantially lower than that of the second train. For example, if the second train runs at 300 ppm Rh and the first train runs at 100 ppm, the output concentration in (stream (17)) is more than enough to supply the needed catalyst for the first train. The rhodium concentration in the first train is controlled by the ratio of (streams (19) to (22)), instead of the ratio of (streams (14) to (15)) as in FIG. 1. The combined outputs from both trains (streams (16) and (22)) are then fed to the same separation zone (7). Optionally, line (23) may be used to enable operation if the second train is down or if either train is operating at reduced production rates.

In one embodiment of the invention, the flow rate of (stream (19)) is higher than the corresponding (stream (14)) in FIG. 1. Therefore, small variations in valve performance will result in a smaller percentage variation in rhodium concentration in the first train.

SPECIFIC EMBODIMENTS OF THE INVENTION

All parts and percentages in the following examples are by weight unless otherwise indicated. Pressures are given as absolute pressure unless otherwise indicated.

Example 1

ASPEN Plus Dynamics™ process simulation software is used to develop an Oxo reaction system process control model for the process of FIG. 1. The catalyst is a typical Rh-bisphosphite catalyst as described in U.S. Pat. No. 4,668,651 and the reaction conditions are essentially those of Example 5 of that patent for butene-1 and Example 9 of that patent for propylene except for the following: a raffinate stream is employed rather than butene-1, the initial target rhodium concentration for the propylene train is 72 ppm Rh, and for the raffinate train the rhodium concentration design target is 260 ppm rhodium, with a Ligand:Rh ratio of >1 for both trains. These are efficient levels that would be used in conventional plants having two completely separate trains, giving high reaction rates, high conversions, and low ligand consumption at design rates for each train.

The basis for the modeling the reactor control system is as follows:
1) The Oxo reaction rate is directly proportional to rhodium concentration at constant temperature.
2) Rhodium concentration in each reactor train is a function of the recycle catalyst mass flow rate and recycle rhodium concentration fed to each reaction train. The liquid volume in each reactor is constant.
3) The recycle rhodium concentration is a function of the olefin feed rates of the two catalyst trains and the concentration of rhodium in each train and thus the ratio of the outputs of each train being fed to the common vaporizer.
4) The effects of items 1 and 2 combine so the oxo reaction rate is a function of the recycle catalyst feed rate and recycle catalyst rhodium concentration.
5) Since ethylene and propylene hydroformylation reaction kinetics are more responsive to changes in the kinetic variables than the raffinate kinetics, the control scheme is designed to control the propylene reactor rhodium concentration, and to keep the temperature of reactor (3) constant, and let the rhodium concentration in the raffinate reaction train vary as necessary. The raffinate reactor temperature can be reduced to offset any higher than design rhodium concentrations.

The results demonstrate conversion and efficiency that are comparable to those for a process running 2 parallel trains that each have their own product-catalyst separation zones. Variation in temperature due to changes in the rhodium concentration caused by changes in the recycle flow are slow, on the order of hours. Therefore, reactor temperature control is done using conventional cooling techniques such as internal cooling coils, external heat exchangers, or both.

The process of the invention allows good control of the rhodium concentration profile. This results in good raw material efficiencies, good control of reactor temperature, and low ligand usage/cost.

Example 2

A series of ASPEN Plus Dynamics™ process simulations are performed using the process of Example 1 to demonstrate the effect of process disturbances on reactor behavior typically observed in commercial operation. These involve reductions in one feed or the other.

The sequence of process feed disturbances is as follows:
  Initially, Propylene and raffinate feed flow rates are at design flow rates.
  At time 4 hours, the raffinate feed flow rate begins a reduction to half of the design flow over a 6 hour ramp period.
  At time 10 hours, the raffinate feed flow is maintained at 50% of design rates.
  At time 40 hours, the raffinate feed flow rate begins a 6 hour increase returning to design rates.
  At time 46 hours, the raffinate is maintained at design flow rates.
  At time 75 hours, propylene feed flow rate begins a ramp for 50% reduction that takes 10 hours.
  At time 85 hours, the propylene feed is maintained at 50% of design flow rate.
  At Time 103 hours, the propylene feed flow rate begins a 10 hour ramp returning to design flow rates.
  At time 113 hours, the propylene feed rate is maintained at design flow rate until completion of the simulation run.

Figure 2:
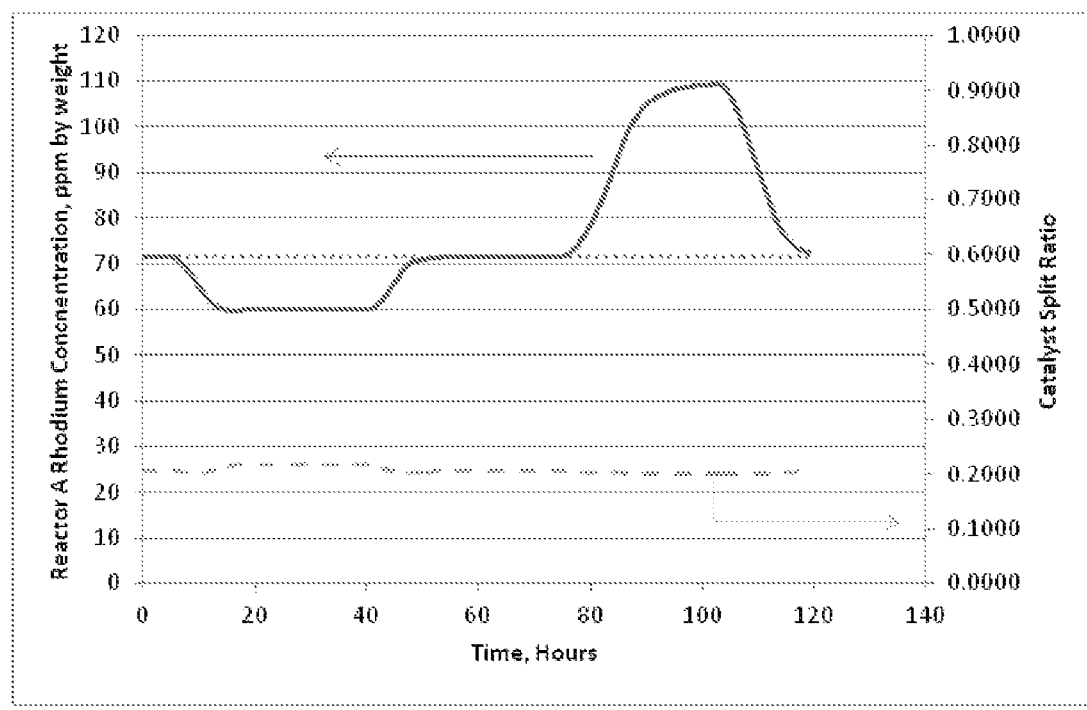
FIG. 2 is a plot of rhodium concentration and the Catalyst Split Ratio in response to process variation.

FIG. 2 shows the variation over time of the rhodium concentration and the Catalyst Split Ratio, which is the mass flow rate of (stream (14)) divided by the mass flow rate of the vaporizer tails flow (stream (9)). FIG. 2 shows the rhodium concentration profiles that result from the process disturbances described above. The catalyst mass flow rates to Reactors 3 and 6 are initially set at design values. Throughout the disturbance sequence, the catalyst flow to Reactor 3 is maintained at the design rate and the flow to Reactor 6 is allowed to vary as dictated by the material balance. No process controls are in place to adjust the catalyst recycle flow rates to respond to process variations that occur in the reaction system, such as the feed flow rate changes illustrated here.

The dotted line is the initial rhodium concentration target (72 ppm), the solid line is the actual rhodium concentration in Reactor (3), and the dashed line is the Catalyst Split Ratio. With a constant design recycle catalyst flow rate (stream (14)) to Reactor 3, the Catalyst Split Ratio changes with vaporizer tails flow rate variations. A constant fraction of the combined reactors' effluent is removed from the vaporizer (7) as product and, as such, a constant fraction of the effluent goes to (stream (9)). With changes in reactant feed rate, the effluent flow rate will change and correspondingly, the flow of (stream (9)) will change. The rhodium concentration will also change given that the fraction of the vaporizer feed from each reactor train changes and the two trains run at significantly different rhodium concentrations. Given these changes, the Reactor (3) rhodium concentration correspondingly varies over a wide range. As FIG. 2 shows, the Reactor (3) rhodium concentration varies between −12 ppm to +30 ppm of the design set point, resulting in poor reactor performance. In particular, for the period of time between 20 and 40 hours when the propylene feed doesn't change, the rhodium concentration drops by 17%, which reduces the reactor efficiency by a comparable amount. A disturbance in the raffinate train has a dramatic impact on propylene train, which is surprising. Then, between 75 to 113 hours when the propylene feed rate is the lowest, the rhodium concentration in the propylene train is the highest, when it is not needed compared to the raffinate train, effectively, the rhodium concentration is reduced in the raffinate stream.

Example 3

Example 2 is repeated except that a different control scheme is employed, as follows:

Maintain the propylene reactors, Reactor (3), at constant temperature and vary the catalyst recycle mass flow rate (stream (14)) to achieve the desired rhodium concentration. The purpose of the control scheme is to maintain the propylene reactors, Reactor (3), at constant reactivity and vary the catalyst recycle mass flow rate (stream (14)) to achieve the desired rhodium concentration. The approach is to "infer" the Reactor (3) rhodium concentration based on the overall material balance and physical volume and geometry of the Oxo reaction system from which the control change is determined. Since the total rhodium inventory is known and fixed, the effect of changes in the operation of each reactor train can be used to predict the performance. The primary variable for each reaction train is the olefin feed, propylene and raffinate for reactors (3) and (6), respectively.

The control scheme consists of the integration two feed-forward controllers to set the recycled catalyst feed to reactor (3) (stream (14)). The first controller takes the propylene feed measurement, multiplies it by a gain factor, and adds a set bias to calculate the required recycled catalyst feed flow rate. This causes the catalyst recycle feed flow rate to be reduced by a predetermined, proportional amount when the propylene feed is reduced a measured amount. The second controller takes the raffinate feed flow measurement, multiplies it by a second gain factor, and adds a bias to calculate a coefficient that is multiplied to the result of the first controller. This multiplier increases the portion of recycle reactor flow going to the propylene reactors during a raffinate feed reduction. The output of this algorithm is sent to the set point of a conventional feedback flow controller to regulate the recycle catalyst feed to the first propylene reactor (3).

Figure 3:
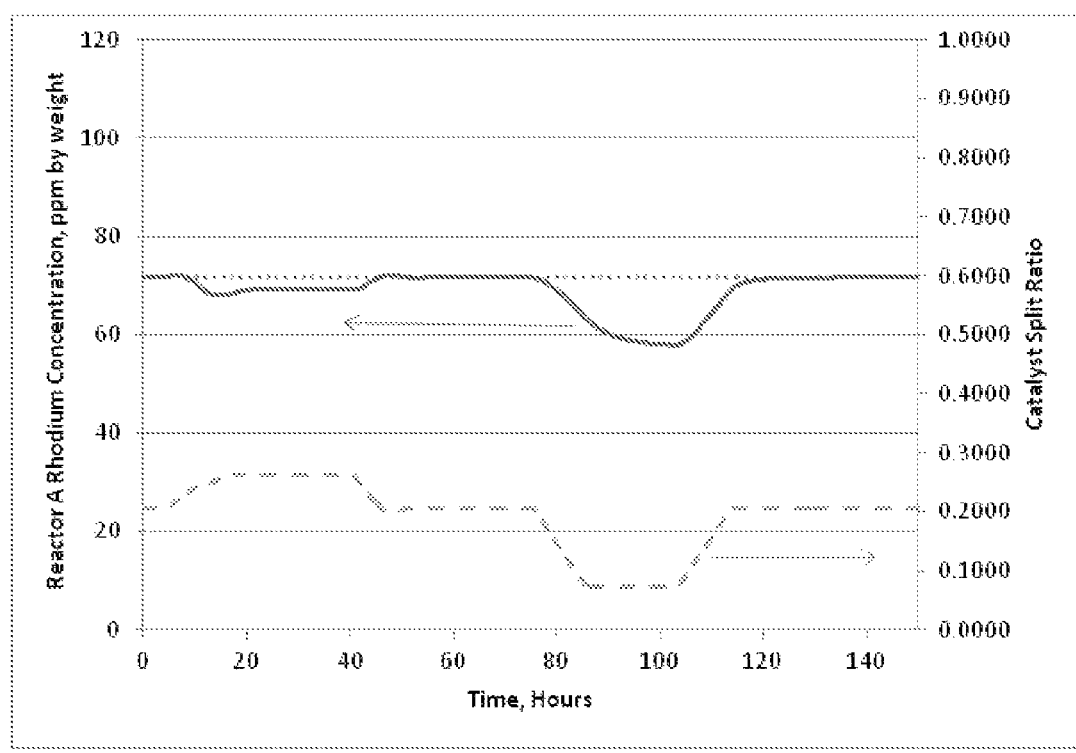
FIG. 3 is plot of rhodium concentration and Catalyst Split Ratio in response to process variation showing improved rhodium control by active flow control.

The performance of the scheme is shown in FIG. 3. It shows a 50% reduction of the raffinate feed followed by the resumption to design flow rates. Following this is the 50% reduction of the propylene feed followed by its resumption to design rates. The controller coefficients were calculated based on the primary effects of feed rates on the process rhodium concentration due to the dilution effect of product formation. If secondary/interacting effects were included, the reactor rhodium variation would have been less. However, the effect of reduced propylene to drop rhodium concentration is seen as advantageous as less rhodium is needed at the lowered production rate.

The Reactor (3) rhodium concentration is controlled within ±4 ppm in the first half of the simulation. After hour 80, the rhodium concentration drop with the propylene feed rate decrease is advantageous because less rhodium is required to achieve the same conversion. This is in contrast to Example 2, where the rhodium level increases to a high level in Reactor (3) and the high rhodium level is of no benefit. Specifically the longer contact time in reactor (3) negates the need for higher rhodium levels, since after ca. 100% conversion, no benefit is obtained from the added rhodium. At hour 103, the propylene feed begins to ramp back to the original value and the rhodium concentration in Reactor (3) increases proportionally back to the original rhodium concentration set point. Controlling the Catalyst Split Ratio is the key to maintaining the proper Reactor (3) rhodium concentration relative to the propylene feed. This gives the best performance in the most sensitive reactor train.

Example 4

Example 2 is repeated except that a different control scheme is employed. The control scheme employs an on-line rhodium analyzer that samples Reactor (3) liquid outlet (stream (16)). The analyzer provides a rhodium concentration value that is used to adjust the catalyst recycle flow (stream (14)) to maintain the desired rhodium concentration in Reactor (3). The results are shown in FIG. 4.

Figure 4:
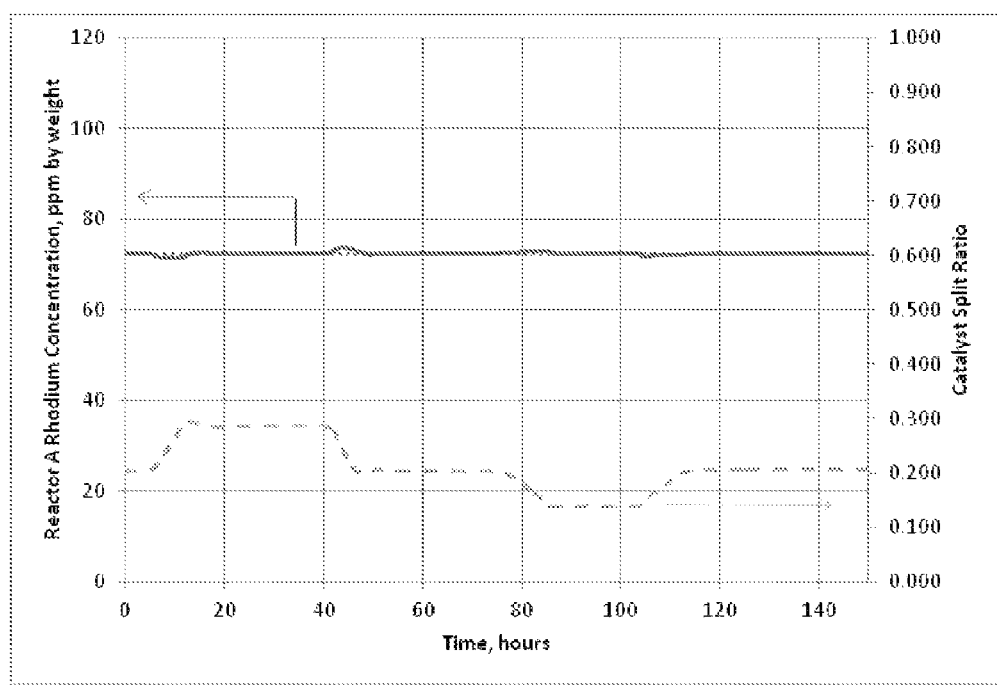
FIG. 4 is plot of rhodium concentration and Catalyst Split Ratio in response to process variation, showing improved rhodium control by on-line rhodium analysis.

FIG. 4 above shows the required Catalyst Split Ratio versus time for a range of propylene and raffinate feed rates. The rhodium analyzer is a reliable on-stream analyzer that is calibrated and periodically updated with manual laboratory analysis according to methods known to those skilled in the art. FIG. 4 shows that the rhodium concentration can be controlled within ±2 ppm in Reactor (3). Since the rhodium concentrations are maintained at design levels, both trains have the optimal rhodium concentrations. Since the rhodium concentration is constant in Reactor (3), a lower reaction temperature can be used in the propylene train to reduce ligand decomposition and aldehyde heavies formation rates if desired without loss of conversion since the residence time is longer when the propylene feed rate is reduced. Similarly, one can lower the reactor operating temperatures in the raffinate reaction train (Reactor 6) to maintain the required reaction rate, based on actual olefin feed rates.

These examples show that, compared to a conventional process that uses separate trains, the invention can be run stably at comparable performance while being able to respond to typical process upsets.

The invention offers the following advantages:
1) Rhodium can be moved from one reactor to another (over a few hours) to match olefin feed rates so that the rhodium concentration is optimized in each reaction train. This feature is also an advantage at startup or whenever a new rhodium catalyst charge is required because only one rhodium catalyst concentration is required for the catalyst charge. Any desired rhodium concentration for a reactor train can be achieved by simply adjusting the recycle catalyst split (between streams 14 and 15) while circulating the catalyst through the reactors and vaporizer for a few hours.
2) The process allows good control of rhodium concentration and operating temperatures, resulting in minimized ligand consumption and heavies formation.
3) The CO and $H_2$ partial pressures within each train can be independently controlled to optimize N:I and avoid side-reactions, e.g., hydrogenation of olefin, ligand decomposition, wherein the optimal conditions may be different for each olefin.
4) The combined catalyst recycle stream will contain residual components from both trains that may help mitigate fouling that would occur in separate but parallel trains. For example, the residual lighter components from the first train may exhibit better solubilities for materials that tend to foul the second train, thus preventing operational difficulties that would occur in totally separate trains.

What is claimed is:

1. A hydroformylation process comprising
   contacting in a first reactor train CO, $H_2$, and a first feed stream comprising an olefin in the presence of a hydroformylation catalyst in a reaction fluid under hydroformylation conditions sufficient to form at least one aldehyde product,
   contacting in at least one additional reactor train CO, $H_2$, and at least one additional feed stream comprising an olefin, in the presence of a hydroformylation catalyst in a reaction fluid under hydroformylation conditions sufficient to form at least one aldehyde product, wherein the additional reactor train is operated in parallel to the first train, and
   removing an effluent stream comprising the reaction fluid from each train and passing the effluent streams from at least 2 reactor trains to a common product-catalyst separation zone,
wherein the olefin composition of the first feed stream is different from the olefin composition of at least one additional feed stream and wherein the hydroformylation conditions in the first reactor train are different from the hydroformylation conditions in at least one additional reactor train.

2. The process of claim 1 further comprising conducting separation in the separation zone to produce a product stream and a catalyst-containing liquid recycle stream, splitting the recycle stream into a first recycle stream and a second recycle stream, and returning the first recycle stream at least partially to one reaction train and returning the second recycle stream at least partially to another reaction train.

3. The process of claim 2 wherein at least a portion of the liquid recycle stream is sent to the second train and the liquid effluent stream from the second train is at least partially sent to the first train and at least partially sent to the product-catalyst separation zone.

4. The process of claim 1 wherein the separating in the common product-catalyst separation zone comprises vaporization, wherein the term vaporization refers to unit operations which are selected from the group consisting of solvent extraction, membrane separation, crystallization, phase separation or decanting, filtration, distillation, and any combination thereof.

5. The process of claim 1 wherein at least one train produces at least one process or effluent stream, and at least part of the process or effluent stream is added to at least one reactor in the other train.

6. The process of claim 1 wherein the second train produces at least one vapor stream, at least part of which is sent to at least one reactor in the first train.

7. The process of claim 1 wherein the effluent stream from the second train is sent to a reaction zone in the first train that is downstream of the first reaction zone in the first train.

8. The process of claim 1 wherein the olefin of the first feed stream is selected from the group consisting of propylene, ethylene, and mixtures thereof.

9. The process of claim 1 wherein the olefin of the first feed stream comprises propylene and the olefin of the second feed stream comprises butene.

10. The process of claim 1 wherein the reaction temperature of at least one reaction zone of each train is controlled in response to a combination of the olefin feed rate, olefin concentration, and concentration of catalytic metal for each relevant zone.

11. The process of claim 1 wherein the concentration of the catalyst within each train is changed in response to changes in the olefin feed rate to either train.

12. The process of claim 1 wherein the catalyst comprises a catalytic metal chosen from Rh, Co, Ir, Ru, Fe, Ni, Os, Pt or Pd and an organophosphorous ligand, and the concentration of catalytic metal in the first reactor train is controlled by measuring the concentration of catalytic metal in at least one reactor and/or at least one of the recycle streams and controlling the flow rate of at least one recycle stream.

13. The process of claim 12 where the concentration of the catalytic metal is measured by atomic absorption, X-ray fluorescence, or inductively coupled plasma-mass spectroscopy and/or measuring in at least one recycle stream components of the catalyst that correlate with the rhodium metal concentration by GC, UV-vis and/or HPLC.

14. The process of claim 2 wherein the amount of the first recycle stream, relative to the second recycle stream, is determined by inferential means based on observed reactor temperature, olefin and CO partial pressures, and total pressure to control the olefin partial pressure to within a desired range.

15. The process of claim 4, wherein the olefin in the first reactor train is lighter than the olefin of the at least one additional reactor train.

* * * * *